United States Patent
Lanier

(10) Patent No.: US 10,065,012 B2
(45) Date of Patent: Sep. 4, 2018

(54) THREE WAY OXYGEN THERAPY CONNECTOR FOR ADMINISTERING NEBULIZED MEDICATION

(71) Applicant: Terri Lanier, Las Vegas, NV (US)

(72) Inventor: Terri Lanier, Las Vegas, NV (US)

( * ) Notice: Subject to any disclaimer, the term of this patent is extended or adjusted under 35 U.S.C. 154(b) by 184 days.

(21) Appl. No.: 14/080,976

(22) Filed: Nov. 15, 2013

(65) Prior Publication Data

US 2014/0137860 A1    May 22, 2014

Related U.S. Application Data

(60) Provisional application No. 61/727,162, filed on Nov. 16, 2012.

(51) Int. Cl.
| | |
|---|---|
| *A61M 16/08* | (2006.01) |
| *A61M 16/06* | (2006.01) |
| *A61M 16/12* | (2006.01) |
| *A61M 16/14* | (2006.01) |

(52) U.S. Cl.
CPC ......... *A61M 16/0833* (2014.02); *A61M 16/06* (2013.01); *A61M 16/12* (2013.01); *A61M 16/14* (2013.01); *A61M 2202/0208* (2013.01)

(58) Field of Classification Search
CPC ..... F16L 41/021; F16L 41/023; F16L 37/008; F16L 37/02; F16L 37/56; F16L 39/00; F16L 39/02; A61M 39/105; A61M 2039/1027; A61M 2039/1083; A61M 2039/1088; A61M 2039/1077; A61M 2039/1094

USPC ..... 128/912; 285/125.1, 126.1, 131.1, 132.1, 285/133.11, 133.21, 133.6; 604/256, 533, 604/538, 284; D24/129
See application file for complete search history.

(56) References Cited

U.S. PATENT DOCUMENTS

| | | | | | |
|---|---|---|---|---|---|
| 3,182,659 | A | * | 5/1965 | Blount | A61M 11/06 128/200.21 |
| D251,734 | S | * | 5/1979 | McCaw | D23/263 |
| 4,240,417 | A | * | 12/1980 | Holever | A61M 16/0465 128/203.12 |

(Continued)

FOREIGN PATENT DOCUMENTS

WO   WO 2008142359 A1 * 11/2008 ............ A61M 16/00

*Primary Examiner* — Lynne Anderson
*Assistant Examiner* — Joseph D Boecker
(74) *Attorney, Agent, or Firm* — Global Intellectual Property Agency, LLC; Jordan Sworen

(57) ABSTRACT

A three-way air flow connector element is provided for operably introducing nebulized medication into an existing oxygen therapy line, which does not require the user to remove the oxygen line to administer the medication. The connector comprises a first and second female connector end and a third male connector end. The first female connector end is adapted to connect to an oxygen line while the third male connector end is adapted to connect to a patient mask, whereby oxygen can be delivered to the patient therethrough. The second female connector end is an operably opened conduit through which a nebulized medication can be introduced to the patient. This end is capped and removably opened by a medical professional, whereby the patient is not deprived of oxygen when connection is made with a nebulizer or similar oral medication delivery system.

4 Claims, 2 Drawing Sheets

(56) References Cited

U.S. PATENT DOCUMENTS

| | | | | |
|---|---|---|---|---|
| 4,385,629 A * | 5/1983 | Wolf, Jr. | A61M 16/0463 | 128/207.14 |
| 4,554,949 A * | 11/1985 | Sell | F16L 37/0985 | 137/899 |
| D294,298 S * | 2/1988 | Bush | D24/110 | |
| 4,827,921 A * | 5/1989 | Rugheimer | A61M 16/08 | 128/202.27 |
| 4,848,331 A * | 7/1989 | Northway-Meyer | A61M 16/0488 | 128/200.26 |
| 4,951,661 A * | 8/1990 | Sladek | A61M 16/0808 | 128/202.27 |
| 5,181,508 A * | 1/1993 | Poole, Jr. | A61M 16/0463 | 128/203.12 |
| 5,230,332 A * | 7/1993 | Strickland | A61M 16/0465 | 128/207.14 |
| 5,382,242 A * | 1/1995 | Horton | A61M 16/0463 | 128/202.27 |
| 5,423,768 A * | 6/1995 | Folden | A61M 1/28 | 604/200 |
| 5,642,726 A * | 7/1997 | Owens | A61M 16/0463 | 128/200.26 |
| 5,701,886 A * | 12/1997 | Ryatt | A61M 16/06 | 128/200.14 |
| D389,571 S * | 1/1998 | Duplesse | D24/110 | |
| 5,730,123 A * | 3/1998 | Lorenzen | A61M 39/26 | 128/200.26 |
| 5,735,271 A * | 4/1998 | Lorenzen | A61M 16/0463 | 128/200.26 |
| D445,182 S * | 7/2001 | Haynes | D24/129 | |
| D448,848 S * | 10/2001 | Clark | D24/112 | |
| 6,615,835 B1 * | 9/2003 | Cise | A61M 16/0463 | 128/200.26 |
| 7,669,595 B1 * | 3/2010 | Mitchell | A61M 11/06 | 128/200.14 |
| 8,042,536 B1 * | 10/2011 | Howey | A61M 11/06 | 128/200.14 |
| 8,444,627 B2 * | 5/2013 | Brewer | A61M 16/0463 | 128/200.24 |
| 8,919,368 B2 * | 12/2014 | Abraham | F16K 13/00 | 137/15.18 |
| 9,072,432 B2 * | 7/2015 | Remmerswaal | A61B 1/018 | |
| 9,186,474 B1 * | 11/2015 | Rollins, III | A61M 16/06 | |
| D747,473 S * | 1/2016 | Martin | D24/129 | |
| 2002/0162554 A1 * | 11/2002 | Loescher | A61M 16/08 | 128/205.24 |
| 2004/0025873 A1 * | 2/2004 | Padgett | A61M 16/0463 | 128/203.12 |
| 2004/0236311 A1 * | 11/2004 | Ishii | A61M 39/20 | 604/533 |
| 2007/0240709 A1 * | 10/2007 | Woolley | A61M 16/08 | 128/200.21 |
| 2008/0087280 A1 * | 4/2008 | Dhuper | A61M 15/009 | 128/200.23 |
| 2008/0210242 A1 * | 9/2008 | Burk | A61M 16/06 | 128/206.21 |
| 2008/0223361 A1 * | 9/2008 | Nieuwstad | A61M 11/02 | 128/200.14 |
| 2009/0194993 A1 * | 8/2009 | Tong | F16L 41/023 | 285/131.1 |
| 2010/0102550 A1 * | 4/2010 | Hama | F16L 41/021 | 285/127.1 |
| 2010/0258114 A1 * | 10/2010 | Cortez, Jr. | A61M 11/005 | 128/200.23 |
| 2011/0114090 A1 * | 5/2011 | Piper | A61M 11/06 | 128/200.23 |
| 2011/0247616 A1 * | 10/2011 | Von Hollen | A61M 16/0816 | 128/203.12 |
| 2015/0352310 A1 * | 12/2015 | Martin | A61M 16/0833 | 128/202.27 |

* cited by examiner

THREE WAY OXYGEN THERAPY CONNECTOR FOR ADMINISTERING NEBULIZED MEDICATION

CROSS REFERENCE TO RELATED APPLICATION

This application claims the benefit of U.S. Provisional Application No. 61/727,162 filed on Nov. 16, 2012, entitled "Multi-Neb Adapter." The above identified patent application is herein incorporated by reference in its entirety to provide continuity of disclosure.

BACKGROUND OF THE INVENTION

Field of the Invention

The present invention relates to oxygen therapy and delivery of medication therewith. More specifically, the present invention pertains to a new and novel air flow connector element that allows for operable connection of a nebulizer in conjunction with an oxygen line, whereby the administrator is not required to disconnect the oxygen line to introduce the nebulizer treatment into the patient's airway.

Many patients require oxygen therapy as a means to treat acute and chronic conditions. Oxygen therapy involves the administration of oxygen at a given percentage to the patient via a mask or breathing tube. The oxygen supplied to the patient is supplied to the patient's lungs, which makes oxygen available to the body for maintaining proper physiological functions. Acute oxygen therapy involves temporarily supplying a patient with increased oxygen flow during an emergency event or during a procedure, where the patient may have undergone a trauma, may be seriously ill, or may be undergoing treatment for a short term condition. Chronic oxygen therapy involves the administration of oxygen for treating more long term conditions, where the therapy is used over longer period of time or on a prescribed basis to treat a given physiological condition.

One type of oxygen therapy is high flow oxygen delivery, in which a patient is delivered a flow of up to 100% oxygen and can be utilized to treat chronic conditions such as sleep apnea, chronic obstructive pulmonary disease (COPD), asthma, and pneumonia. High flow oxygen delivery systems are capable of supplying the patient's entire ventilatory demand through a mask or nasal prongs, wherein the air can be humidified, temperature controlled and delivered using a number of different delivery devices.

One common problem that exists is the need to introduce a nebulized medication in the oxygen line when the patient is receiving all of their oxygen from the oxygen therapy system. If the system is not equipped with a nebulizer port or means of introducing the medication upstream, the medical professional must remove the mask temporarily to administer the medication. This causes a deprivation of oxygen and is not at all convenient for the health care professional or the patient.

The present invention is directed to an oxygen delivery system connector element that accommodates the use of a nebulizer. The device comprises a three-way adapter that connects a nebulizer with high-flow oxygen and oxygen line. The device enables a patient to receive a nebulizer treatment while maintaining an appropriate amount of oxygen at the same time, which prevents a drop in oxygen saturation. The device delivers high-flow oxygen and nebulizer treatments together and does not require the patient to be deprived of oxygen or the professional to waste time swapping between oxygen and nebulizer treatments when a nebulizer is required. This eliminates the therapist struggle and hassles with the current methods of trying to give oxygen and nebulizer treatments, and will not compromise the delivery of the nebulizer treatment.

Description of the Prior Art

Devices have been disclosed in the prior art that relate to airway connectors, oxygen delivery devices, and nebulizers. The following is a list of devices deemed most relevant to the present disclosure, which are herein described for the purposes of highlighting and differentiating the unique aspects of the present invention, and further highlighting the drawbacks existing in the prior art.

One such device is U.S. Pat. No. 5,396,883 to Knupp, which discloses a T-shaped valve assembly for the administration of medication by way of a nebulizer for a patient who is attached to a ventilator. The valve assembly includes a control knob for operably controlling the pathway between a nebulizer cup and a first tube, wherein the first tube carries oxygen to the patient and the nebulizer cup is adapted to provide medication to the patient through the pathway. The control knob operates a valve that opens and closes the pathway to the nebulizer cup. The Knupp device, while disclosing an oxygen therapy and nebulizer attachment device, provides a T-shaped fitting having an operable valve, wherein a nebulizer is attached in-line with an oxygen line. The present invention contemplates a Y-shaped fitting and a valveless assembly. The administrator attaches a nebulizer to the otherwise capped conduit of the fitting to deliver the medication to the patient, whereafter this conduit can be sealed for oxygen delivery only.

Another device is U.S. Pat. No. 6,328,030 to Kidwell, which discloses a nebulizer assembly for engagement in a ventilator circuit, wherein a coupler is provided having two end ports and a lateral port to connect to a nebulizer reservoir. A valve is provided within the assembly for operably allowing the nebulizer treatment to enter the air pathway through the assembly. Similar to the Knupp device, the Kidwell device describes a valve in order to operate and to administer the nebulizer medication. The present invention provides a capped conduit that is accessible by a healthcare professional for connecting a nebulizer in line with an oxygen line.

U.S. Pat. No. 4,951,661 to Sladek discloses an three-way adapter for quick-connecting a nebulizer to a ventilator hose without interrupting the flow of oxygen to the patient during connection. The device comprises a cylindrical lower cavity for receiving the nebulizer, an upper cavity supporting a valve assembly therein, and a conduit for the ventilator oxygen to pass to the patient. Similar to the aforementioned devices, the Sladek device uses a valve to connect the nebulizer. The present invention contemplates a simpler design that includes three connections, one of which is securable until attachment to a nebulizer device is required. The device is simple and inexpensive, requiring no moving parts that would add to the cost.

Finally, U.S. Design Pat. No. D294,175 to Briggs and D389,571 to Duplesse disclose T-junctions for use with nebulizers and breathing tubes. These articles disclose two configurations of a T-connector for securing an air line and a nebulizer. The structure and design of these devices differ in elements from the prior art, which includes a first and second female fitting and a male fitting to split an air line and provide access to a nebulizer connection when operably attached thereto.

The present invention describes a new and novel attachment for oxygen therapy and for operable delivery of nebulized medication. The device permits regular use of the oxygen line and offers a port for introducing nebulized medication therethrough, without disconnecting a patient's airway during the process. The present invention is substantially divergent in design elements from the prior art, and consequently it is clear that there is a need in the art for an improvement to existing oxygen therapy connector devices. In this regard the instant invention substantially fulfills these needs.

SUMMARY OF THE INVENTION

In view of the foregoing disadvantages inherent in the known types of oxygen therapy connector devices and accessories now present in the prior art, the present invention provides a new, three-way connector element that can be utilized for providing convenience for the user when introducing nebulized medication into the oxygen line of a patient.

It is therefore an object of the present invention to provide a new and improved oxygen therapy connector device that has all of the advantages of the prior art and none of the disadvantages.

It is another object of the present invention to provide an oxygen therapy connector device that includes an oxygen line connection, an oxygen mask connection, and a nebulizer connection.

Another object of the present invention is to provide an oxygen therapy connector device that includes a nebulizer connection having an operably securable cap that allows for connection to a nebulizer without removing the patient's oxygen line, whereafter medication can be administered therethrough.

Yet another object of the present invention is to provide an oxygen therapy connector device having a first and second female connector and a third male connector, the male connector adapted to attach to the breathing mask of a patient.

Another object of the present invention is to provide an oxygen therapy connector device that includes no valves, special connectors, or moving parts that add complexity and cost.

A final object of the present invention is to provide an oxygen therapy connector device that may be readily fabricated from materials that permit relative economy and are commensurate with durability.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
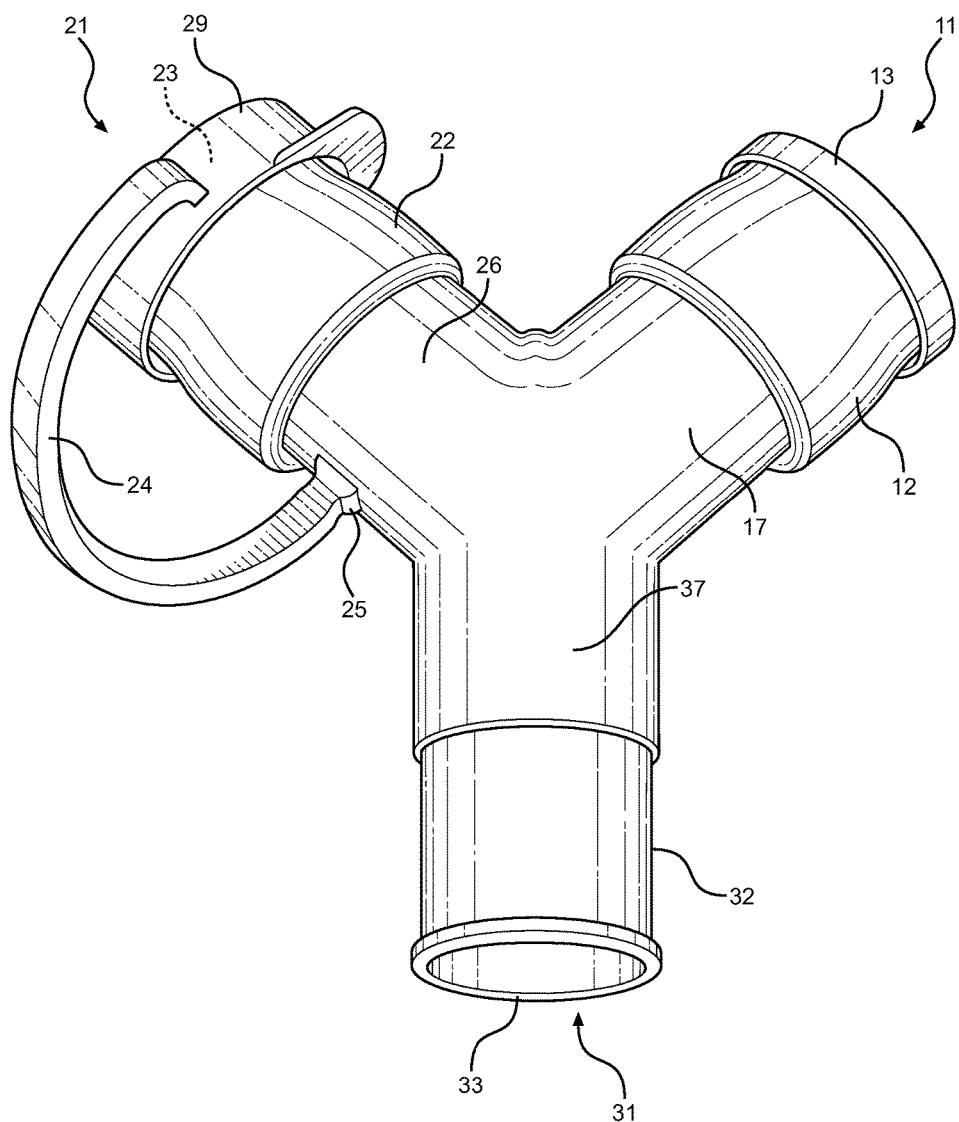
FIG. 1 shows a frontal perspective view of the three way connector of the present invention.

Reference is made herein to the attached drawings. Like reference numerals are used throughout the drawings to depict like or similar elements of the three way connector of the present invention. For the purposes of presenting a brief and clear description of the present invention, the preferred embodiment will be discussed as used for operably introducing a nebulizer in-line with a patient's oxygen line without disconnecting the same. The figures are intended for representative purposes only and should not be considered to be limiting in any respect.

Figure 2:
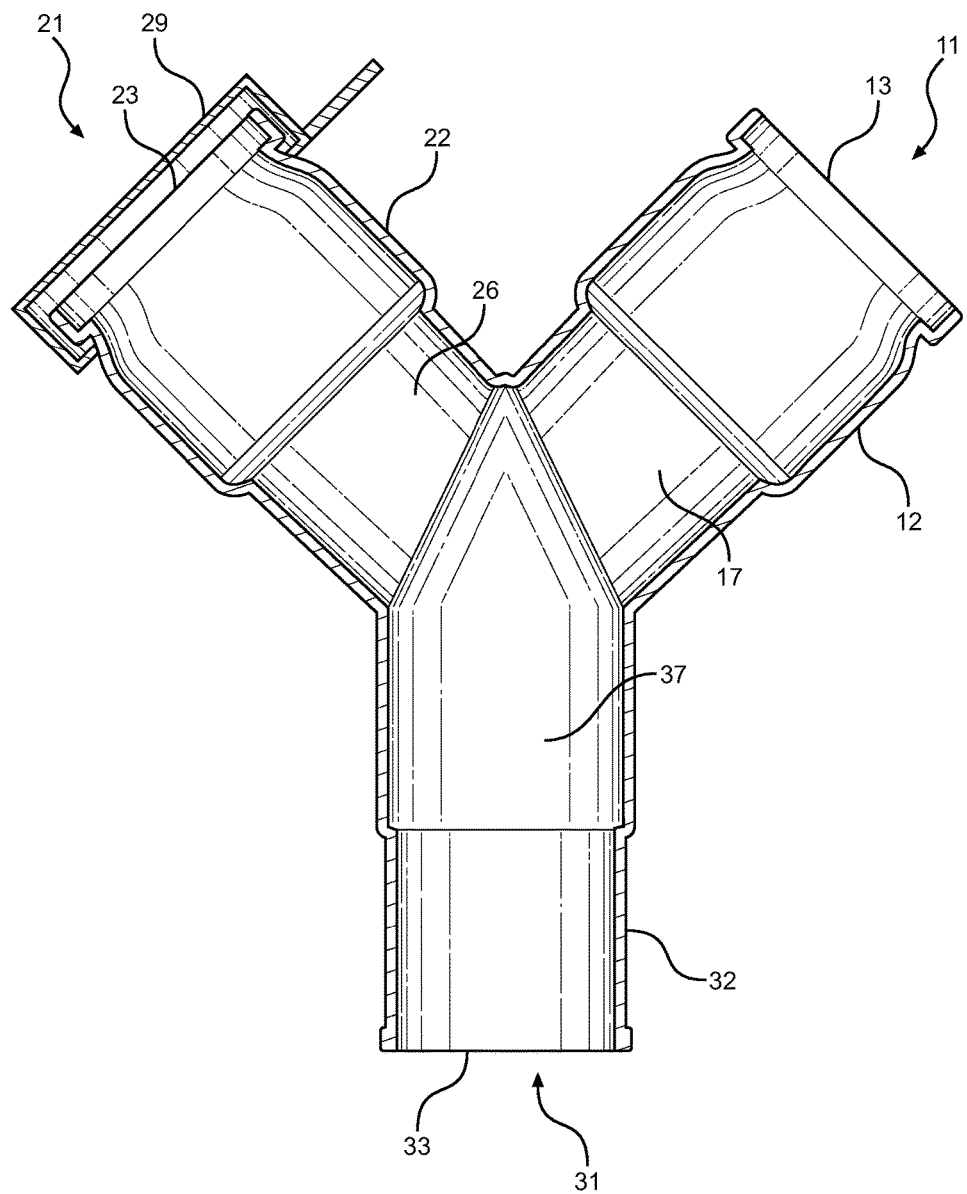
FIG. 2 shows a cross sectional view of the three way connector of the present invention.

Referring now to FIGS. 1 and 2, there is a frontal and a cross section view of the three way connector element of the present invention. The connector element comprises three ports: a first oxygen port 11, a second nebulizer port 21, and a third oxygen mask connector port 31. The three ports form a three way, Y-shaped connector, whereby the oxygen line port 11 and the nebulizer port 21 are angularly connected and combine into a single pathway leading to the oxygen mask port 31 therebelow. The device is adapted to be secured in-line with a patient's oxygen therapy line, whereby a nebulizer port 21 is offered such that the pathway of oxygen is not disturbed during nebulizer treatments.

The oxygen line port 11 of the present invention comprises a conduit 17 having an open termination 13 and an outwardly protruding end that is of a widened cross section. This widened end forms a female connector 12 that is adapted to accept the male end of an oxygen tube thereinto. Once connected, oxygen flows into the port opening 13, through the oxygen conduit 17 and through the oxygen mask connector port 31 to the patient.

In a similar fashion, the nebulizer port 21 of the present invention includes a female connector end 22. However, the nebulizer port 21 includes an opening 23 that is operably closed and opened by way of a securable cap 29, which forms an air-tight seal over the nebulizer port opening 23 to prevent oxygen leakage or drawing of ambient air into the connector interior. The cap 29 is tethered 24 to the external surface of the nebulizer port conduit 26 and is permanently secured 25 thereto. In this way, the cap 29 can be removed and moved to the side of the opening 23 without fear of the cap 29 falling to the ground or becoming misplaced.

The nebulizer port 21 and the oxygen line port 11 converge together and form into the oxygen mask connector port 31 to create a Y-shaped connector. The oxygen mask connector port 31 comprises an elongated conduit 37 that is adapted to carry oxygen from the oxygen line port 11 and any nebulized medication entered into the nebulizer port 21. The oxygen mask conduit 37 terminates at an opening 33 adapted to connect to a patient's oxygen mask or a tube attached thereto. This port 31 includes a male connector 32 that comprises a reduced thickness termination that allows the port 31 to be inserted into the female connector of the patient's oxygen mast.

When installed, the present invention provides a healthcare specialist or caretaker to administer nebulized medication through an oxygen line without first removing the oxygen line from the patient. The cap 29 of the nebulizer port 21 can be removed to expose its open end 23, wherethrough the nebulized medication is inserted after the nebulizer is connected thereto. An uninterrupted stream of oxygen flows through the oxygen line port 11 and through the mask connector port 31 to the patient as the nebulizer is connected and while it is administering medication to the stream of oxygen. The two ports 21 and 11 form together and create a Y-connection that mixes the medication and oxygen before being ingested by the patient.

Referring specifically to FIG. 2, there is shown a cross section view of the three way connector of the present invention. This view illustrates the open interior of the connector, wherein no moving parts, valves, or special connectors are necessary to mix nebulized medication into an oxygen line connected to a patient oxygen mask. Further illustrated are the removable cap 29 and its pull tab, which facilitates removal of the cap therefrom. Once removed, a male nebulizer connector can be inserted into the female nebulizer port 21 to combine the medication with the incoming oxygen through the oxygen line port 11 that is traveling to the patient through the mask port 31.

The connector of the present invention comprises a simple adapter that is well suited for introducing a nebulizer into a high flow oxygen treatment line. The Y-shaped adapted allows for the simultaneous connection of a nebulizer and oxygen delivery system to the patient, whereby the nebulizer treatment can be operably initiated without ceasing the oxygen therapy. With both devices connected, the present invention enables a patient to receive a nebulizer treatment while maintaining an appropriate percentage of oxygen at the same time, which prevents a drop in oxygen saturation.

In operation, a user can apply a reservoir bag to the oxygen port and a nebulizer to the nebulizer port of the device. The user can then attach both items to a separate flow meter and use as needed. The mask can be made from medical plastic quality, high-density, FDA-approved polyethylene or other suitable materials. In this way, the present invention enables people to receive medication from a nebulizer and oxygen at the same time.

It is submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A nebulizer-oxygen line connector, comprising:

a substantially Y-shaped connector having a first port and a second port converging into a third port;

the first port comprising a first open conduit including a first open end, wherein an outer diameter of the first open end is greater than an outer diameter of the first open conduit;

the second port comprising a second open conduit including a second open end, wherein an outer diameter of the second open end is greater than an outer diameter of the second open conduit;

the second port further comprising a cap, the cap removably securable over the second open end of the second port, wherein the cap is attached to the second open conduit;

the third port comprising a third open conduit terminating at a third open end, wherein an outer diameter of the third open end is greater than an outer diameter of a male connector of the third port;

wherein the first open end is disposed in a first distinct plane, the second open end is disposed in a second distinct plane, and the third open end is disposed in a third distinct plane;

wherein the first port is symmetrical to the second port about a central axis of the third open conduit;

wherein the first port includes an outer sidewall that tapers inwardly toward the first open end, and wherein the second port includes an outer sidewall that tapers inwardly toward the second open end.

2. The nebulizer-oxygen line connector of claim 1, further comprising:

wherein the first open end of the first port is configured to accept a male connector of an oxygen line therein;

wherein the second open end of the second port is configured to accept a male connector of a nebulizer therein; and wherein the third open end of the third port is configured to receive a female connector of an oxygen mask.

3. The nebulizer-oxygen line connector of claim 2, wherein the first port and the second port are oriented so as to form an angle less than one hundred eighty degrees therebetween.

4. The nebulizer-oxygen line connector of claim 1, wherein each of the first distinct plane, the second distinct plane, and the third distinct plane are non-parallel to each other.

* * * * *